US006682699B2

(12) United States Patent
Mustacich et al.

(10) Patent No.: US 6,682,699 B2
(45) Date of Patent: *Jan. 27, 2004

(54) REDUCED POWER CONSUMPTION GAS CHROMATOGRAPH SYSTEM

(75) Inventors: Robert V. Mustacich, Santa Barbara, CA (US); James F. Everson, Santa Barbara, CA (US)

(73) Assignee: RVM Scientific, Inc., Santa Barbara, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 09/796,508

(22) Filed: Mar. 2, 2001

(65) Prior Publication Data

US 2001/0009647 A1 Jul. 26, 2001

Related U.S. Application Data

(63) Continuation of application No. 08/791,466, filed on Jan. 27, 1997, now Pat. No. 6,217,829.

(51) Int. Cl.$^7$ ................................................ G01N 30/02
(52) U.S. Cl. .......................... 422/89; 96/104; 96/106; 422/90; 422/91; 422/92
(58) Field of Search ................ 96/104, 106; 210/198.2, 210/696; 422/20, 89–92; 436/161; 73/23.35, 23.39, 23.42, 61.52

(56) References Cited

U.S. PATENT DOCUMENTS

| 3,032,953 A | 5/1962 | Micheletti |
| 3,159,996 A | 12/1964 | Norem |
| 4,176,542 A | 12/1979 | Redding |

(List continued on next page.)

FOREIGN PATENT DOCUMENTS

| EP | 445967 | 9/1991 |
| EP | 745845 | 12/1996 |
| JP | 61-29760 | 2/1986 |
| SU | 1458809 | 2/1989 |
| WO | WO 91/00131 | 1/1991 |

OTHER PUBLICATIONS

E.U. Ehrmann, et al., "Novel Column Heater for Fast Capillary gas Chromatography," J. of Chromatographic Science, vol. 34, Dec. 1996, pp. 533–539.

R. Lloyd, "Instrumentation for Automated Thermal Desorption–Pyrolysis Capillary Gas Chromatography," J. Chromatography, vol. 284, No. 2, Feb. 1984, pp. 357–371.

C. Gahler, et al., "Fiber Optic Temperature Sensor Using Sampled Homodyne Detection," Applied Optics, vol. 30, 1991, pp. 2938–2940.

(List continued on next page.)

*Primary Examiner*—Arlen Soderquist
(74) *Attorney, Agent, or Firm*—Rosenberg, Klein & Lee (57) ABSTRACT

This invention provides a reduced power consumption gas chromatograph system (10) which includes a capillary gas chromatograph column member (12) which contains a chemical sample to be analyzed. The gas chromatograph system further includes a heating mechanism (16) which extends throughout the length of the capillary gas chromatograph column member (12) and surrounds both the member (12) and a temperature sensing mechanism (14) which is mounted adjacent to the column member (12). The temperature sensing mechanism (14), the heating mechanism (16) and the column member (12) form a chromatograph column assembly (20) which includes a coiled section (28) where the components are tightly packed with respect to each other and allows for a reduced power consumption for temperature programming miniature gas chromatography column assemblies.

16 Claims, 4 Drawing Sheets

U.S. PATENT DOCUMENTS

| | | | |
|---|---|---|---|
| 4,474,889 | A | 10/1984 | Terry et al. |
| 4,484,061 | A | 11/1984 | Zelinka et al. |
| 4,726,822 | A | 2/1988 | Cates et al. |
| 5,005,399 | A | 4/1991 | Holtzclaw et al. |
| 5,014,541 | A | 5/1991 | Sides et al. |
| 5,298,225 | A | 3/1994 | Higdon |
| 5,544,276 | A | 8/1996 | Loux et al. |
| 5,611,846 | A | 3/1997 | Overton et al. |
| 5,846,292 | A | 12/1998 | Overton |
| 6,217,829 | B1 * | 4/2001 | Mustacich et al. ............ 422/89 |

OTHER PUBLICATIONS

A. Appleyard, et al., "Intrinsic Optical Fiber Temperature Sensor Based on the Differential Absorption Technique," Review of Scientific Instruments, vol. 61, 1990, pp. 2650–2654.

W. Maswadeh, et al., "New General of Hand–Held, Disposable Gas Chromatography Devices," pp. 56–59.

E. Overton, et al., "A New Portable Micro Gas Chromatograph For Environmental Analysis," pp. 207–212.

E. Overton, et al., "New Horizons in Gas Chromatography: Field Applications of Microminiaturized Gas Chromatographic Techniques," Trends in Analytical Chemistry, vol. 13, No. 7, 1994, pp. 252–257.

D. Hawker, et al., "Portable, Automatic Gas Chromatograph For Natural Gas Analysis," Oper. Sect. Proc.–Am. Gas Assoc., 1984, pp. 674–678.

T. Anderbrugge, et al., "Portable Gas Chromatograph For Examination of Mixtures of Gases," Gaswaerme Int., vol. 41, Jan. 1992, pp. 29–33.

M. Burns, "High–Speed Portable Gas Chromatography," Erdol Und Kohle–Erdgas–Petrochemi Vereinight Mit Brennstoff–Chemie, vol. 47, Mar. 1994, pp. 80–84.

V, Jain, et al., "Fast Temperature Programming on Fused–Silica Open–Tubular Capillary Columns by Direct Resistive Heating," J. Chromatographic Science, vol. 33, Jan. 1995, pp. 55–59.

P. Holland, et al., "Correlated Column Micro Gas Chromatography Instrumentation For the Vapor Detection of Contraband Drugs in Cargo Containers," Proc. SPIE–Int. Soc. Opt. Eng., vol. 2276, 1994, pp. 79–86.

Y. Guan, J. of Fushun Petroleum Institute, vol. 16, 1996, pp. 43–46.

P. Holland, et al., "Handheld GC Instrumentional for Chemical Wapons Convention Treaty Vertification Inspections," Field Screening Methods for Hazardous & Toxic Chemicals, vol. 1, 1995, pp. 229–235.

* cited by examiner

REDUCED POWER CONSUMPTION GAS CHROMATOGRAPH SYSTEM

This patent application is a continuation application of Ser. No. 08/791,466, filed on Jan. 27, 1997, now U.S. Pat. No. 6,217,829, issued on Apr. 17, 2001.

BACKGROUND OF THE INVENTION

1. Field of the Invention

The present invention relates to gas chromatography systems for generally continuously sampling chemical samples and detecting desired compounds therefrom. In particular, the subject invention is directed to gas chromatographic column assemblies for temperature programmed analyses. More in particular, the subject invention relates to gas chromatograph column assemblies where power savings are achieved through optimized packing of capillary gas chromatograph column members with temperature sensors and heating wires which substantially increases the internal contact of such components with themselves and each other while reducing the amount of surface area of these components in contact with the surroundings. Still further, this invention relates to gas chromatograph systems which include assemblies of capillary gas chromatograph column members, temperature sensing mechanisms and heating mechanisms formed into a gas chromatograph column assembly which is positionally located in a manner to optimize thermal effects and produce an overall low power consumption system.

2. Prior Art

High performance gas chromatography has typically required the use of large laboratory instruments using large amounts of electrical power in their operation. This is especially the case for the standard practice of temperature programming a chromatographic separation in which the temperature of the oven containing the gas chromatography column is steadily increased to extend the range of gas chromatography separation capability. The large power required to heat and temperature program gas chromatography ovens has limited the capability of gas chromatography for use in portable instrumentation and especially in hand-portable instrumentation used in the field. Without large external power sources or large batteries, gas chromatography design and operations have been limited largely to non-temperature programming applications in small, lightweight portable instruments.

Additional requirements for gas chromatography technology to be practical in small portable instruments is for the technology to be compatible with and use commercially available gas chromatography capillary column technology. Since the use of capillary columns has become standard practice in laboratory gas chromatography instrumentation, a large number of capillary columns are now commercially available which offer a wide range of separation capabilities. The wide range of separation capabilities has been made possible through variation of the chemical compositions of the polymers which coat the inner walls of the capillary gas chromatography columns. Choice may now be had from many polymer coatings that are commercially available in capillary gas chromatography columns having standard thicknesses, column lengths, and column inner diameters to optimize the chemical separations required of the gas chromatography. The ability to readily use this commercially available gas chromatography column technology in small portable gas chromatography instruments is desirable for the practical realization of similar analytical capabilities in portable or small gas chromatography instruments.

The temperature programming of capillary gas chromatography columns is standardly practiced by electronic control of the temperature of an oven containing the gas chromatography column. To achieve rapid and uniform temperature response of the gas chromatography column assembly to temperature changes in the oven, capillary gas chromatography columns are standardly packaged by winding the columns on a wire frame support. The winding of the columns on the wire frame support provides extensive surface contact of the capillary gas chromatography column with the heated air in the oven for rapid temperature equilibration of the capillary gas chromatography column with the oven air. In laboratory gas chromatography ovens, the air within the oven is typically mixed with a fan to achieve temperature uniformity within the oven. Laboratory gas chromatography instruments typically consume power on the order of kilowatts for temperature programming and are power limited to temperature ramping rates approximating 10's of ° C./min or less, especially at higher operating temperatures. While smaller, more portable gas chromatography instruments have been manufactured which have smaller ovens, such still require powers on the order of 1 kW or more for temperature programming, especially when ramping rates of 10's of ° C./min are required for fast analysis times.

Reductions in gas chromatography oven size to that of a small heated compartment large enough to contain a short length of gas chromatography column have been made for the purposes of reducing power consumption and reducing instrument size. The resulting gas chromatography instruments are typically operated isothermally to avoid the power consumption associated with temperature programming, but this greatly constrains the analytical capabilities of such gas chromatography instrumentation. One case in which low power temperature programming has been implemented is described by Maswadeh et al. in "New Generation of Hand-Held, Compact, Disposable Gas Chromatography Devices," Field-Portable Chromatography and Spectrometry workshop, Jun. 3–5, 1996, Snowbird, Utah, pp. P56–P59. In this case a palm-size gas chromatography module was demonstrated which consumes 15W of power for temperature programming at a 0.75° C./s ramp rate. A short ramp with a maximum temperature of 60° C. served to limit power consumption by the module.

The need for fast temperature programming of miniature chromatographic analysis instrumentation is described by Sides and Cates in U.S. Pat. No. 5,014,541. They describe the requirement to raise the temperature of the capillary gas chromatography column from 50° C. to 120° C. within 20 seconds to achieve their analysis objectives. They accomplish this with a miniature gas chromatography column assembly in which the standard gas chromatography oven is replaced by a tubular heat conductor support on which the gas chromatography column is wound. A heating element within the tubular support is used for temperature programming. While this instrument achieves a gas chromatograph of small size, the power consumption is on the order of 1 kW and a portable power generator is a recommended option for portable operation of this commercial instrument.

The importance of reducing the thermal mass of gas chromatography column assemblies for the rapid heating was recognized by Norem in U.S. Pat. No. 3,159,996. This invention consisted of a glass tube with three parallel bores and sufficient length to contain a heater wire, a resistance thermometer wire (a type of temperature sensor), with the remaining bore coated on the inside to function as a gas chromatography column. While such a device could have a smaller thermal mass than a small, conventional gas chromatography oven, a large amount of power will still be required to heat the sizable mass of glass tubing.

Another way to significantly reduce power consumption with a miniature gas chromatography is by reducing the electrical heating and sensing elements of gas chromatography ovens to miniature forms and integrate them with a capillary gas chromatography column. U.S. Pat. No. 5,005,399 achieves this by using a thin-film coated capillary gas chromatography column wound on a mandrill consisting of an insulating material. Electrical current passed through the thin film surrounding the gas chromatography column is used to resistively heat the column. While this approach uses far less power than heating a conventional gas chromatography oven, it still requires significant power to heat the gas chromatography column because of the large surface area of the gas chromatography column in contact with the mandrill material since this insulating support is also heated through contact with the heating element. A serious shortcoming of this approach is the difficulty of fabricating annular thin film coatings of substantial length having sufficient uniformity and freedom from defects. The thermal mass of the gas chromatography column plus contacting insulation is large enough that currents on the order of 1 ampere or more are typically required for fast temperature programming using battery voltages such as 12 volts. The conduction of such large currents in thin film resistive heaters requires the films to be substantially free of defects. While thickness non-uniformity results in uneven heating, typical defects in thin films due to microcontamination, particulates, abrasion from handling, or stresses and fractures due to bending (such as coiling the column) cause local hot spots and thin film breakdown resulting in failure of the heater element. A further difficulty with this approach is that it is not compatible with the use of commercially available gas chromatography column technology; special thin film resistor-coated versions of each gas chromatography column of interest would have to be manufactured requiring large scale, omni-directional precision deposition of very high quality films. Given the technical problems with the handling, operating and manufacturing of precision thin film resistive heaters of this scale, this is a serious difficulty.

While not claiming low power operation, a similar approach by U.S. Pat. No. 4,726,822 relies on annular thin film heater and insulator layers to miniaturize a heated capillary gas chromatography column assembly. In addition to the handling, operating and manufacturing impracticalities discussed in the preceding paragraph with respect to U.S. Pat. No. 5,005,399, the close spacing of multiple thin films present additional difficulties.

Another approach to reducing power consumption by a capillary gas chromatography column assembly has been published by Holland, et al. in "Handheld Gas Chromatography Instrumentation for Chemical Weapons Convention Treaty Verification Instrumentation," Field Screening Methods for Hazardous Wastes and Toxic Chemicals, Vol. 1, Air & Waste Management Association, Pittsburgh, 1995, pp. 229–235. In this approach a gas chromatography capillary column is placed inside a length of small plastic tubing along with coaxial heater and sensor wires. This gas chromatography assembly uses far less power than the power required by commercial gas chromatography ovens. Typical powers required for temperature programming this assembly are still on the order of 10's of watts per meter of column length for fast, short gas chromatography column configurations reported by Overton and Carney in "New Horizons in Gas Chromatography: Field Applications of Microminiaturized Gas Chromatographic Techniques," Trends in Analytical Chemistry, Vol. 13, 1994, pp. 252–257, and by Overton, et al. in "A New Portable Micro Gas Chromatograph for Environmental Analysis," in Field Screening Methods for Hazardous Wastes and Toxic Chemicals, Vol. 1, Air & Waste Management Association, Pittsburgh, 1995, pp. 207–212. Much lower power consumption is required for battery powered fast temperature programming by small portable gas chromatography instruments. While this approach permits the use of commercially available gas chromatography capillary columns, the difficulty of threading capillary gas chromatography columns, heater wires, and sensor wires into small plastic tubing limits the practical assembly lengths to several meters.

SUMMARY OF THE INVENTION

A reduced power consumption gas chromatograph system is provided which includes a capillary gas chromatograph column member having a predetermined length containing a chemical sample therein. A temperature sensing mechanism is provided for measuring a temperature of the chemical sample contained within the capillary chromatograph column member with the temperature sensing mechanism located adjacent the gas chromatograph column member. A heating mechanism is provided for heating the chemical sample contained within the gas chromatograph column member with the heating mechanism positionally located around the capillary chromatograph column member. The capillary gas chromatograph column member in combination with the temperature sensing mechanism and further in combination with the heating mechanism forms a gas chromatograph column assembly.

It is a basic object of this invention to provide a gas chromatograph column assembly which achieves fast, temperature programming rates with a low power consumption.

It is a further object of the subject invention to provide an innovative packing of a capillary gas chromatograph column member with a temperature sensor and heater wires to increase the internal contact of such components within a coiled section while reducing the fraction of each component surface area exposed at the periphery of the coiled section.

It is still a further object of this invention to optimally reduce the amount of the packed component's surface area within the coiled section which is exposed directly to air or insulating surroundings.

It is a still further object of this invention to allow heat exchange and conservation of energy within the packed combination of a gas chromatography column member, heating mechanism and temperature sensing mechanism.

It is another object of this invention to provide an overall gas chromatography column assembly internally heated and consisting of a packed, low thermal mass set of components in which the outer surface of the assembly has a small surface area compared to the total surface area of the components within the assembly for reducing both the heat loss to the surroundings and the heat required to raise the temperature of the components.

A still further object of this invention is to provide a system having the ability to readily incorporate any standard commercially available gas chromatography capillary column member into a low power miniature gas chromatography column assembly.

DESCRIPTION OF THE PREFERRED EMBODIMENTS

Referring now to FIGS. 1–7, there is shown reduced power consumption gas chromatograph system 10 which is particularly useful in miniature and portable gas chromatograph instruments. In overall concept, the reduced power consumption is embodied by a unique packing and location scheme of a capillary gas chromatograph column member 12 in combination with a temperature sensing mechanism 14 and a heating mechanism 16 which, as will be shown in following paragraphs, substantially increases the internal contact of such components with themselves and each other while simultaneously reducing the amount of surface area of these components in contact with the external environment to reduced operational power requirements.

The reduced power consumption gas chromatograph system 10 includes in general, injection device 18 for introducing chemical samples into gas chromatograph column assembly 20 comprised of gas chromatograph column member 12, temperature sensing mechanism 14, and heating mechanism 16. The components of gas chromatograph column assembly 20 is clearly seen in FIG. 3.

Detection device 22 is coupled to the exit section of gas chromatograph column assembly 20 and measures, as well as analyzes chemicals present in the vapor exiting gas chromatograph column assembly 20. A number of commercially available detection devices 22 exist and are not important to the inventive concept as herein described, however, such may include flame ionization, flame photometry, mass spectrometry, ion mobility, electron capture, and other ionization techniques.

A programmable computer 24 is coupled into system 10 to provide control of injection device 18, detection device 22, as well as the parameters associated with reduced low power consumption gas chromatograph system 10 within gas chromatograph column assembly 20.

It is to be understood that the subject reduced power consumption chromatograph system 10 is contemplated for use with a number of well-known injection devices 18, detection devices 22, as well as possibly remote monitors. However, computer 24, injection device 18, and detection device 22 as well as the electronics packages associated therewith may assume a variety of circuit and structural configurations well-known in the art which are not germane to the present invention with the exception that they provide proper chemical samples to gas chromatograph column assembly 20 as well as appropriate heating and control mechanisms. Thus, in the interest of clarity, further discussion of any electronics packages, computer 24, detection device 22, or injection device 18 will be omitted since they do not form a part of the subject invention concept. Additionally, the entrance and exit regions of gas chromatograph column assembly 20 are generally heated and maintained at elevated temperatures to prevent stoppage or slowing of analytes through possible cold spots in gas chromatograph column assembly 20, however, such heaters are well-known in the art and may at times even be included with injection device 18 and detection device 22, but are not depicted in the Figures since such do not form part of the invention concept as herein described.

Figure 1:
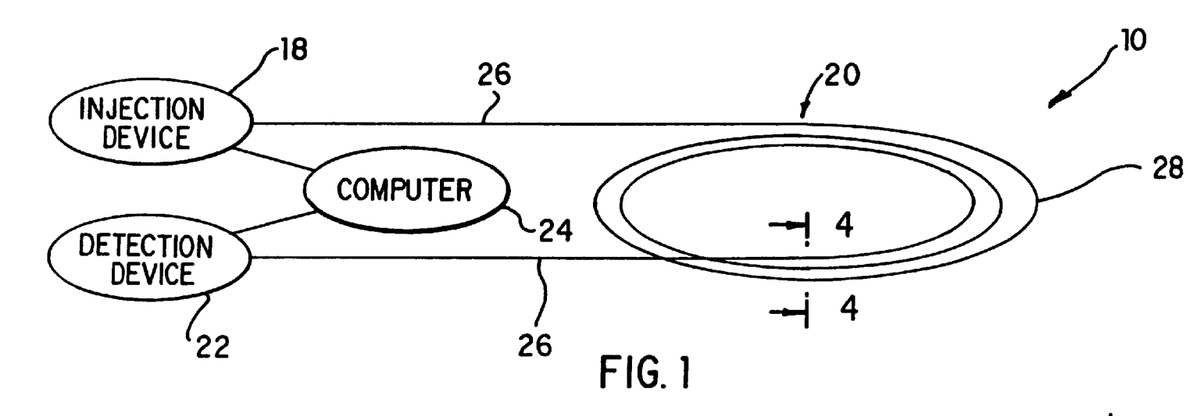
FIG. 1 is a schematic representation of the reduced power consumption gas chromatograph system showing a coiled section in a gas chromatograph column assembly.
Figure 3:
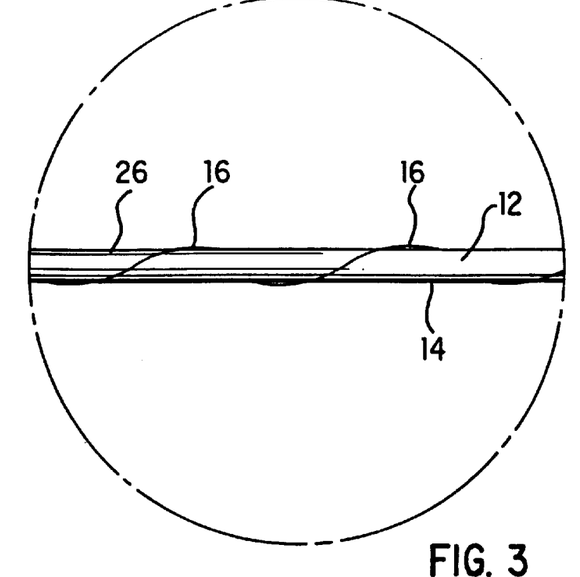
FIG. 3 is a schematic representation of a lead section of the gas chromatograph column assembly showing the components thereof.
Figure 4:
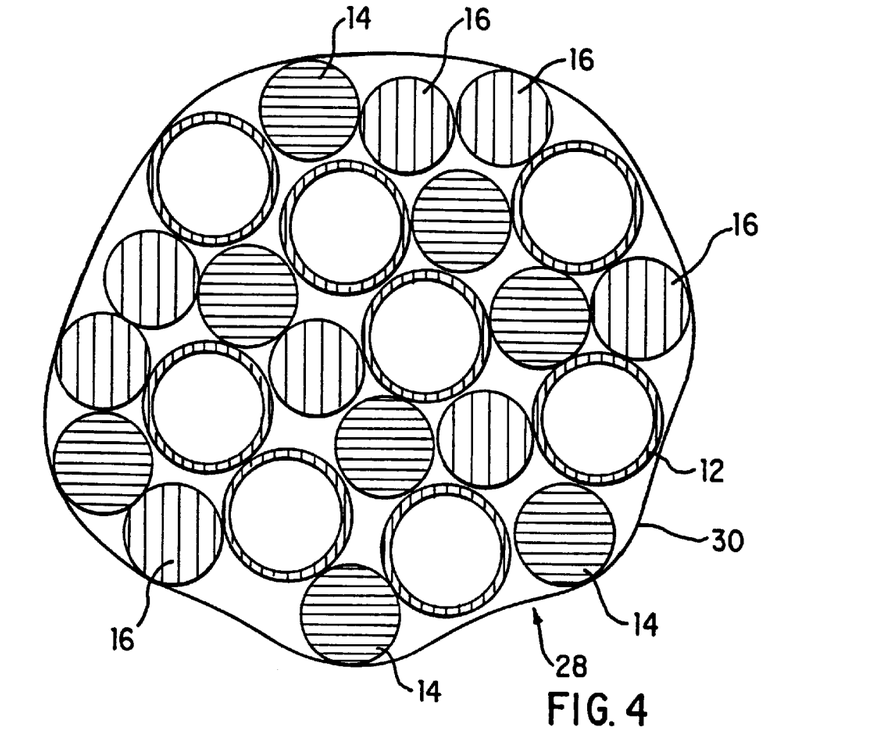
FIG. 4 is a cross-section of the coiled section of the gas chromatograph column assembly taken along the Section Line 4—4 of FIG. 1.

Referring specifically to FIGS. 1, 3, and 4, there is shown gas chromatograph column assembly 20 which includes lead section 26 (both entry and egress sections being labelled with the same element number), and coiled section 28 of gas chromatograph column assembly 20. Lead sections 26 and coiled sections 28 are composed of gas chromatograph column member 12, temperature sensing mechanism 14, and heating mechanism 16, as is shown in FIG. 3. Capillary gas chromatograph column member 12 has a predetermined length containing a chemical sample therein. Gas chromatograph column member 12 may be formed of a fused silica or some like material.

Heating mechanism 16 heats the chemical sample contained within gas chromatograph column member 12. Heating mechanism 16 may be positionally located around capillary chromatograph column member 12, as is shown in FIG. 3. Heating mechanism 16 may take the form of an insulated wire member wound around gas chromatograph column member 12 in a co-axial manner and in particular may be helically wound around the combination of gas chromatograph column 12 and temperature sensing mechanism 14, as further shown in FIG. 3. A winding of heating mechanism or heater wire 16 reduces the difficulty in handling the components when hand coiling of coiled section 28 is accomplished. In general, heating wire or heating mechanism 16 may correspond to a pitch of 10° or less for the helical winding. Pitches of 10° or less were not found to adversely affect the power requirements for low power consumption gas chromatograph assemblies 20, however, extensive winding of heater wires 16 at pitch angles greater than about 20° C. resulted in increased power consumption by the gas chromatograph column assembly 20. Heater wires 16 in actual use may be composed of 0.005" diameter Chromel wire having approximately 0.003" insulation formed on the exterior of the heater wire 16. Use of such insulated wire members 16 is advantageous in that such provides a low thermal mass per unit length.

Temperature sensing mechanism 14 forming a component of gas chromatograph column assembly 20 measures the temperature of the gas sample contained within capillary chromatograph column member 12 with the temperature sensing mechanism 14, in the preferred embodiment, extending substantially throughout the predetermined length of, and located adjacent gas chromatograph column member 12, as is shown in FIG. 3. As is seen, temperature sensing mechanism 14 may be located in adjacent positional relationship with capillary gas chromatograph column member 12 and may be mounted within the wound coils of heating wire 16. Experimentation with differing types of temperature sensing mechanisms 14 show that low power results could be achieved using a number of well-known temperature sensing mechanisms 14 as long as the particular temperature sensors were of a low thermal mass design. Such temperature sensing mechanisms 14 applicable to reduced power consumption gas chromatograph system 10 include resistance temperature devices such as alloys in the form of insulated fine wires which provide for a change in resistance as a function of temperature. Resistance temperature devices generally provide a distributed measurement of the temperature along the entire length of the temperature sensor. It is within the scope of this invention to use other types of temperature sensing elements providing a more local or point measurement of the temperature and such may be in the form of a thermocouple used in place of the temperature sensor element shown in the Figures. In such a configuration, gas chromatograph column assembly 20 would consist of capillary gas chromatograph column member 12, heater mechanism or heater wire 16, and a point temperature sensor introduced in the coiled section 28 of column assembly 20 to measure the temperature of the coiled components. Substitution of temperature sensors having larger thermal masses such as thermocouples are formed of approximately 0.010" diameter wires was found during experimentation to slightly increase the power requirements required for temperature programming of very low thermal mass assemblies which is the result of larger heats required to raise such temperatures to a local temperature.

As shown in FIG. 4, coiled section 28 of column assembly 20 is enclosed within enclosure housing 30. In this manner, coiled section 28 of gas chromatograph column assembly 20 is thermally isolated from an external environment. Enclosure housing 30 encapsulates coiled section 28 of gas chromatograph column assembly 20 and may be in the form of a sheath formed around coiled section 28.

Sheath or enclosure housing 30 may be formed with foil wrappings of coiled section 28 as well as placement of coiled section 28 within thermally insulating materials. Thermally insulating materials forming enclosure housing 30 were tested in the form of high thermal protection composite fiber ceramic insulation commercially available from Lockheed Missiles and Space Company located in Sunnyvale, Calif. High thermal protection composite fiber ceramic insulation having a designation HTP-16 was used successfully in providing low power consumption and such included a low thermal conductivity approximating 0.54 Btu-in./ft.$^2$-hr.-° F. with a low specific heat approximating 0.2 Btu per/lb.-° F.

Figure 2:
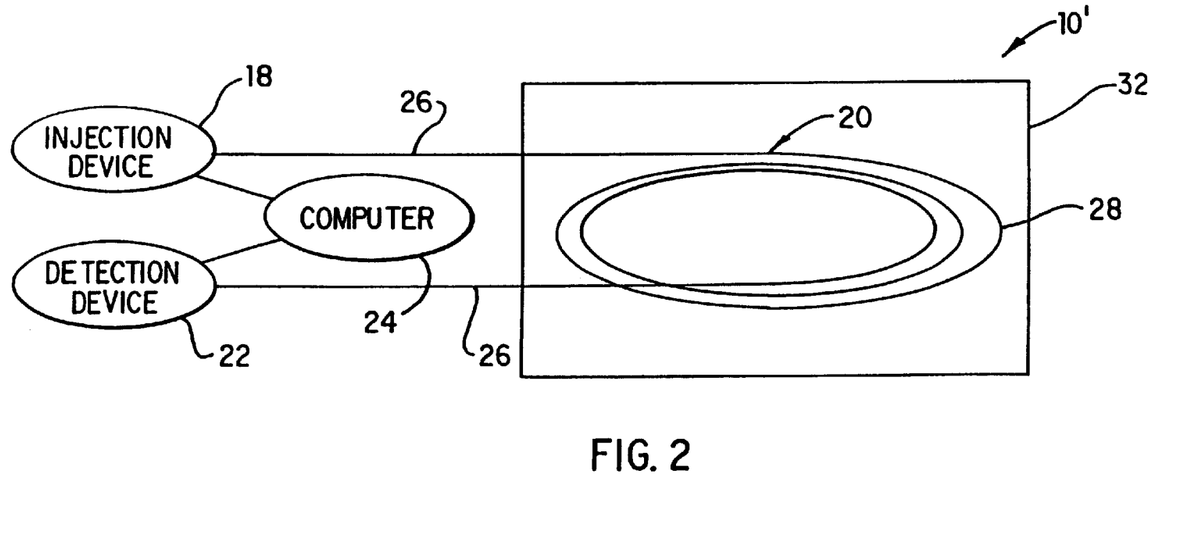
FIG. 2 is a schematic representation of an embodiment of the reduced power consumption gas chromatograph system shown in FIG. 1 wherein the coiled section of the gas chromatograph column assembly is located within a vacuum environment.

An embodiment of reduced power consumption gas chromatograph system 10' is shown in FIG. 2 where gas chromatograph column assembly 20 is contained within vacuum container 32 for the purposes of increasing thermal isolation between gas chromatograph column assembly 20 and the external environment.

A series of tests were run for reduced power consumption gas chromatograph system 10 or 10' where coiled section 28 of gas chromatograph column assembly 20 included a sheath or housing 30 formed of a foil wrap as previously described in an open air environment, a foil wrap contained within a vacuum, and assembly 20 having an insulating housing material as previously discussed. For the experimentation with the high thermal protection composite fiber ceramic insulation, the packed coil assembly 28 was placed between 2×2×0.5" pieces of HTP-16 with each of the pieces containing a circular groove to hold the packed coil assembly 28. In order for the insulated enclosure assembly to cool quickly so that another temperature programmed analysis may be started, it is necessary to cool the heated components at the end of a temperature programmed analysis. It was found that small openings of approximately 1–2 mm in diameter in the enclosures placed along the path of a circular groove containing the packed coil 28 of gas chromatograph capillary column assembly 20 provided sufficient air passages with a miniature electric fan being used to allow rapid cooling. The introduction of the openings through the insulating enclosures was not found to significantly increase the power required for temperature programming of the capillary gas chromatograph column assembly 20. For comparison with the power requirements for tubing-jacketed gas chromatograph column designs, the identical capillary gas chromatograph column assemblies 20 were placed in a 1.0 meter length of Teflon tubing having an inner diameter approximating 0.063" and a wall thickness approximating 0.012" following the designs of the prior art Holland, et al. systems (1995) previously discussed.

The low power gas chromatograph capillary column assembly 20 was temperature programmed by using a heater circuit in which the temperature sensor 14 served as a feedback control element. The circuit applied a current to the heater wire 16 as long as the temperature sensed by the temperature sensor 14 was below a target temperature. By using a computer-generated voltage ramp for the target temperature, the heater circuit then followed the computer-generated ramp resulting in a temperature program ramp of the subject gas chromatograph capillary column assembly 20. A temperature program using the heater circuit was selected to simulate the temperature program used by the prior art Maswadeh, et al. (1996) previously discussed. The current required by the heater circuit was measured using a digital ammeter and recorded in a processor and the average power required during a thirty second heating ramp was then calculated. The following Tables 1 and 2 summarize the average power required for 0.75° C./s for (1) a temperature program from 32° C.–55° C. and (2) a temperature program from 32° C.–180° C. The average power required for these conditions is summarized in the following Tables:

TABLE 1

| POWER REQUIRED FOR 0.75° C./s FROM 32° C.–55° C. | |
|---|---|
| TYPE | AVERAGE POWER (WATTS) |
| Subject System with Foil Wrap in Air | 0.52 |
| Subject System with Foil Wrap in Vacuum | 0.53 |
| Subject System within Insulated Housing Material | 0.60 |
| Prior Art System, Holland, et al. (1995) Using Teflon-Tubing Jacketed Components | 3.4 |
| Prior Art System for Low Power Gas Chromatograph System of Maswadeh, et al. (1996) | 15.0 |

Table 1 clearly indicates that the power required is a factor of 30 lower than the low power temperature programming results achieved by the prior art Maswadeh, et al. (1996) system. An 85% reduction in power was also demonstrated relative to the low power, tubing-jacketed designs reported by the prior art Holland, et al. (1995) systems. Similar results are obtained with the subject reduced power consumption gas chromatograph system 10 in air and in vacuum using a foil wrapped packed coil assembly 20. Power requirements using the insulating enclosure was also seen to be low with an average power of 0.60 watts but not as low as the foil wrapped assembly 20 which showed an average power of 0.52 in air and 0.53 in vacuum.

The temperature program used for the results in Table 1 was limited to relatively low temperatures for the gas chromatography-ion mobility spectrometer application described in the prior art Maswadeh, et al. (1996) system. Larger temperature ranges are generally used in programming to achieve a wider range of chemical separations using gas chromatography. However, as the programming temperatures increase relative to the ambient temperatures, heat conduction to the surroundings increases and the resulting power required for programming also rises. In order to demonstrate the low power requirements of the subject reduced power consumption gas chromatograph system 10, the upper temperature limit of the programs used were extended to 180° C. The average power results are summarized in the following Table 2 which once again shows a dramatic decrease in the average power between the known prior art and the subject invention concept.

TABLE 2

POWER REQUIRED FOR 0.75° C./s FROM 32° C.–180° C.

| TYPE | AVERAGE POWER (WATTS) |
| --- | --- |
| Subject System with Foil Wrap in Air | 2.0 |
| Subject System with Foil Wrap in Vacuum | 1.6 |
| Subject System Within Insulated Housing Material | 2.6 |
| Subject System Without Enclosure Sheath in Air | 3.1 |
| Prior Art System, Holland, et al. (1995) Using Teflon-Tubing Jacketed Components | 18.0 |

Figure 5A:
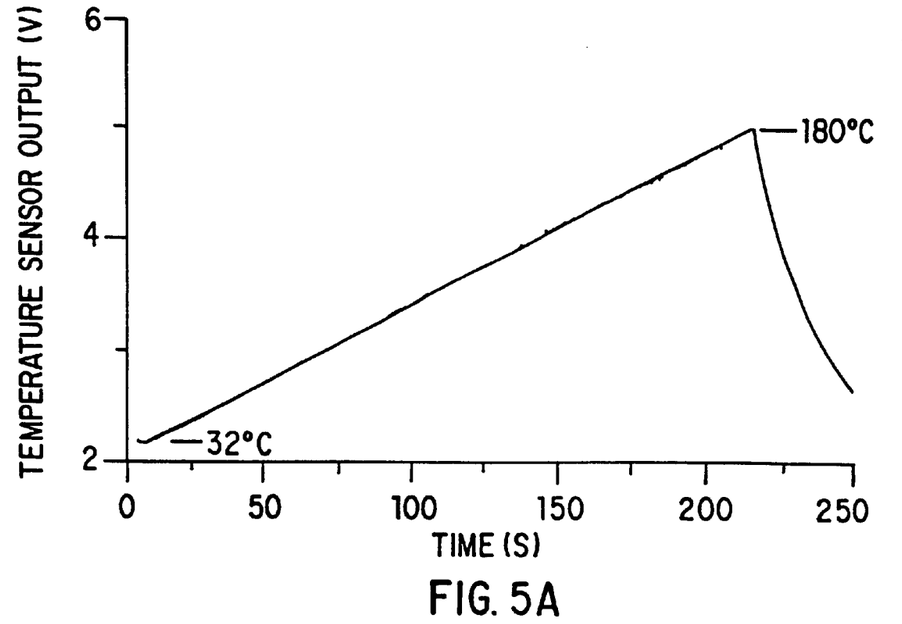
FIG. 5 is a graph of the reduced power consumption gas chromatograph system showing temperature programming of a low power gas chromatograph capillary column assembly from 32° C.–180° C. at a rate of 0.75° C./s.
Figure 5B:
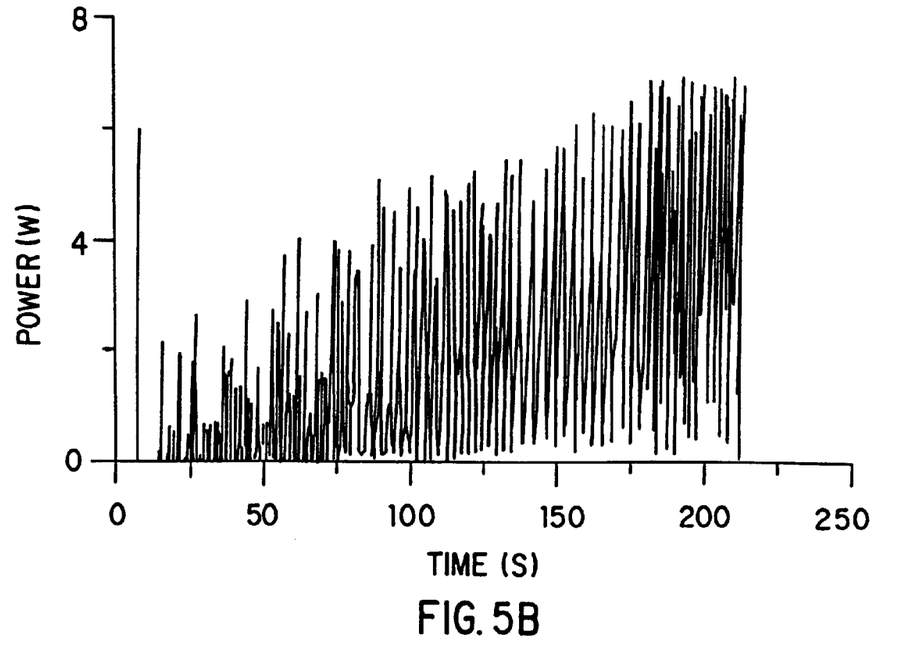

Referring to FIG. 5, such provides a temperature sensor output and power vs. time for heating of the foil wrapped gas chromatographic capillary column assembly 20 in air at a rate of 0.75° C./s shown as the initial example in Table 2. FIG. 5 is directed to the raw data for the instantaneous power used by the internal heater wire 16 in the lower portion of the graph. The temperature programmed ramp reported by the temperature sensor 14 is shown in the upper trace of the graph. The temperature ramp is substantially linear and the average power consumed during the ramp is approximately 2.0 watts. Since the ramping rate was the same as the rate used for the experiments shown in Table 1, integration and averaging of the power during the first thirty seconds of this ramp resulted in a power approximating 0.5 watts as shown in Table 1.

Figure 6:
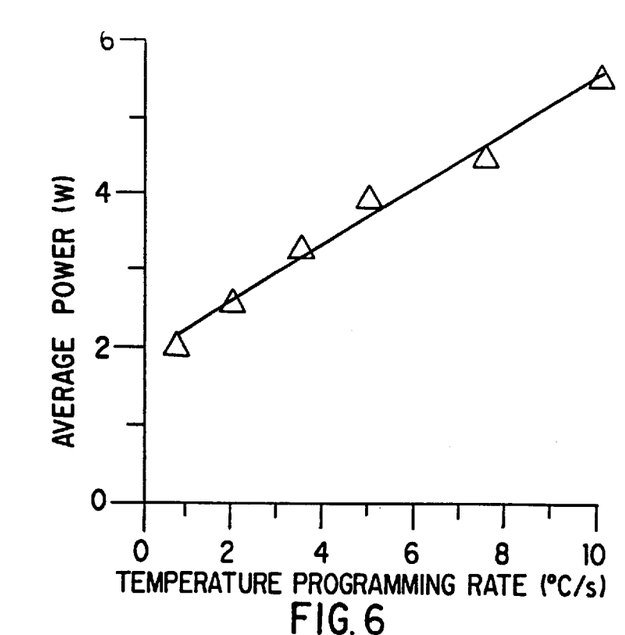
FIG. 6 is a graph showing average power required to temperature program a linear ramp between 32° C.–180° C. with the reduced power consumption gas chromatograph system for a plurality of different temperature programming rates; and, FIG. 7 is a graph showing a fast gas chromatography data for the separation of some semi-volatile alkane hydrocarbons using the subject reduced power consumption gas chromatograph system.
Figure 7:
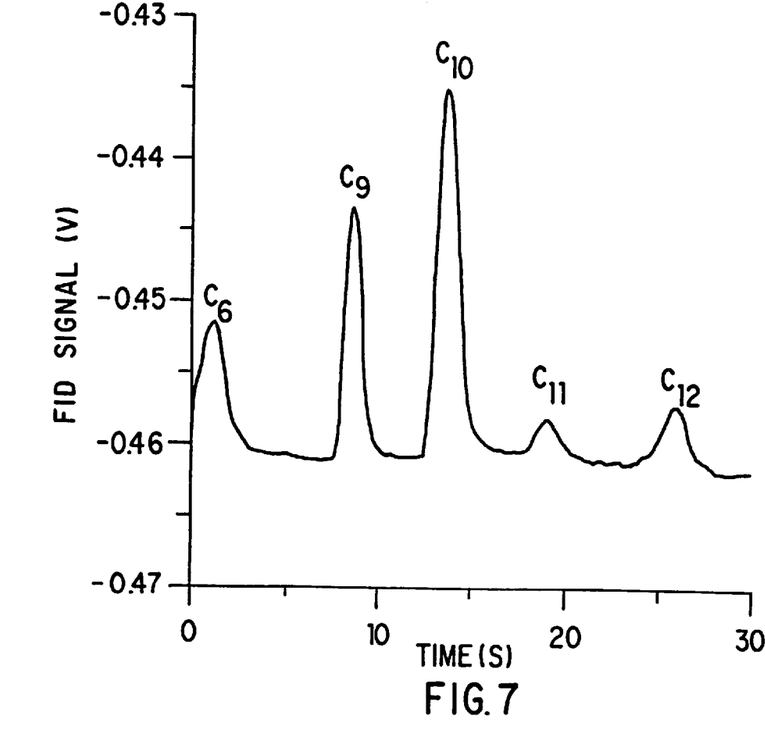

As is known, the average power required during a temperature program increases with increasing ramping rates. The average power required for the foil wrapped low power gas chromatograph capillary column assembly 20 in air at different ramping rates between 32° C. and 180° C. is shown in the graph of FIG. 6. Relatively small increases in the average power are required for large increases in the temperature programming rate for such an assembly. Because of the shorter time for heat conduction to the surroundings, fast temperature programming rates can consume less total power. Importantly, the subject system 10 reduces average power requirements to a level that allows fast ramping possible even in battery-operated portable instruments which further reduces the total power requirements while increasing the speed of temperature programmed analyses.

An example of fast chromatography using a 1 meter, HTP-insulation enclosed low power gas chromatography capillary column assembly 20 is shown in FIG. 6. The assembly contained a 1 meter Sulfur-AT column member purchased from Alltech Associates, Inc. of Deerfield, Ill. having an internal diameter approximating 0.32 mm. A column flow rate of 10 mL/min of helium was used for chromatography with this short column which was directly connected to a flame ionization detector. A temperature program of 2° C./s for 30 seconds duration was used with a starting temperature of 40° C. Such conditions provided fast, low resolution separation of semi-volatile alkane hydrocarbons between nonane ($C_9$) and dodecane ($C_{12}$) in less than 30 seconds.

Although this invention has been described in connection with specific forms and embodiment thereof, it will be appreciated that various modifications other than those discussed above may be resorted to without departing from the spirit or scope of the invention. For example, functionally equivalent element may be substituted for those specifically shown and described, proportional quantities of the elements shown and described may be varied, and in the formation method steps described, particular steps may be reversed or interposed, all without departing from the spirit or scope of the invention as defined in the appended claims.

What is claimed is:

1. A reduced power consumption gas chromatograph system having reduced power consumption during temperature programming, comprising:

(a) a capillary gas chromatograph column member having a lead section and a plurality of adjacently positioned coiled loops forming a coiled section containing a chemical sample therein;

(b) a temperature sensor to measure a temperature of said chemical sample contained within said capillary chromatograph column member, said temperature sensors being located adjacent said coiled loops forming said gas chromatograph column member coiled section; and, (c) a heating element for heating said chemical sample contained within said gas chromatograph column member, said heating element being positionally located adjacent said capillary chromatograph column member loops and in proximity thereto for effecting substantially uniform heat transport to said chemical sample, said heating element being located adjacent each of said coiled loops, said capillary gas chromatograph column member, said temperature sensor and said heating element forming a gas chromatograph column assembly having a respective length defined by the summation of the lengths of each of said loops and cross-section thereof defined by said combined cross-section of said plurality of coiled loops, said temperature sensor and said heating element, said capillary gas chromatograph column member, said temperature sensor and said heating element combination of said plurality of coiled loops contacting each other within said coiled section, said temperature sensor and heating element being positionally located within said coiled section adjacent at least two of said coiled loops, said cross-section of the gas chromatograph column assembly coiled section having a sufficient number of loops for maximizing internal surface contact therebetween thereby providing substantially uniform heat transfer transport throughout said cross-section of said plurality of coiled loops, thereby minimizing power consumption.

2. The reduced power consumption gas chromatograph system as recited in claim 1 where said temperature sensor extends substantially throughout said lead section and said coiled section of said chromatograph column member.

3. The reduced power consumption gas chromatograph system as recited in claim 1 where said heating element includes an insulated wire member.

4. The reduced power consumption gas chromatograph system as recited in claim 3 where said insulated wire member is formed of an alloy of chromium or nickel.

5. The reduced power consumption gas chromatograph system as recited in claim 1 where said coiled section of said gas chromatograph column assembly includes at least two coils of said combination of said gas chromatograph column, said temperature sensor and said heating element.

6. The reduced power consumption gas chromatograph system as recited in claim 1 where said temperature sensor is located in axially aligned relationship with said capillary gas chromatograph column member.

7. The reduced power consumption gas chromatograph system as recited in claim 6 where said temperature sensor measures temperature throughout at least a portion of a length of said temperature sensor.

8. The reduced power consumption gas chromatograph system as recited in claim 6 where said temperature sensor is a resistance thermal device.

9. The reduced power consumption gas chromatograph system as recited in claim 1 where at least said coiled section of said gas chromatograph column assembly is thermally isolated from an external environment.

10. The gas chromatograph column assembly as recited in claim 9 including an enclosure housing encapsulating said coiled section of said gas chromatograph column assembly.

11. The gas chromatograph column assembly as recited in claim 10 where said enclosure housing is formed of a thermally insulating material.

12. The gas chromatograph column assembly as recited in claim 10 where said enclosure housing is a sheath formed around said coiled section.

13. The gas chromatograph column assembly as recited in claim 12 where said sheath is formed of a thermally conducting foil member.

14. The gas chromatograph column assembly as recited in claim 13 where said sheath encapsulated coiled section is hermetically sealed within a vacuum chamber.

15. The gas chromatograph column assembly as recited in claim 10 where said enclosure housing forms a vacuum chamber for isolating said coiled section from an external environment.

16. The gas chromatograph column assembly as recited in claim 1 where said temperature sensor is at least one thermocouple.

* * * * *